(12) United States Patent
Sevrain

(10) Patent No.: US 8,827,944 B2
(45) Date of Patent: Sep. 9, 2014

(54) ANTI-CLOGGING VENTRICULAR CATHETER FOR CEREBROSPINAL FLUID DRAINAGE

(75) Inventor: Lionel C. Sevrain, West Palm Beach, FL (US)

(73) Assignee: Lers Surgical, LLC, West Palm Beach, FL (US)

( * ) Notice: Subject to any disclaimer, the term of this patent is extended or adjusted under 35 U.S.C. 154(b) by 474 days.

(21) Appl. No.: 12/676,404

(22) PCT Filed: Sep. 10, 2008

(86) PCT No.: PCT/US2008/075823
§ 371 (c)(1),
(2), (4) Date: Apr. 22, 2010

(87) PCT Pub. No.: WO2009/036039
PCT Pub. Date: Mar. 19, 2009

(65) Prior Publication Data
US 2010/0222732 A1    Sep. 2, 2010

Related U.S. Application Data

(60) Provisional application No. 60/971,060, filed on Sep. 10, 2007.

(51) Int. Cl.
*A61M 5/00* (2006.01)
*A61M 27/00* (2006.01)
*A61B 5/03* (2006.01)
*A61M 5/142* (2006.01)

(52) U.S. Cl.
CPC ............ *A61M 27/006* (2013.01); *A61M 27/002* (2013.01); *A61B 5/031* (2013.01); *A61M 5/14276* (2013.01)
USPC .................................................. 604/8; 604/9

(58) Field of Classification Search
CPC ............ A61M 27/006; A61M 27/002; A61M 5/14276; A61B 5/031
USPC .............................. 604/8–10, 19–22, 540–543
See application file for complete search history.

(56) References Cited

U.S. PATENT DOCUMENTS

| 4,351,333 | A | * | 9/1982 | Lazarus et al. ................. 604/28 |
| 4,655,745 | A | * | 4/1987 | Corbett ........................ 604/540 |
| 4,767,400 | A | * | 8/1988 | Miller et al. ..................... 604/8 |
| 5,405,316 | A | * | 4/1995 | Magram ........................... 604/8 |
| 5,531,673 | A |   | 7/1996 | Helenowski |

(Continued)

OTHER PUBLICATIONS

International Preliminary Report on Patentability, issued Mar. 25, 2010 (published Mar. 25, 2010) during the prosecution of International Application No. PCT/US2008/075823.

(Continued)

*Primary Examiner* — Philip R Wiest
(74) *Attorney, Agent, or Firm* — Novak Druce Connolly Bove + Quigg LLP

(57) ABSTRACT

A novel ventricular catheter designed to reduce CSF shunt obstruction is disclosed comprising a tip using a membrane without any opening and capable of filtering the CSF. When the CSF flows through the membrane, neither tissue (choroid plexus, blood cells, tumor cells, suctioned ependymal tissue) nor proteins can break through the membrane, making this ventricular catheter capable of preventing obstruction from tissue invasion but also preventing clogging from protein precipitation, coagulation or flocculation along the downstream shunt system.

17 Claims, 10 Drawing Sheets

(56) References Cited

U.S. PATENT DOCUMENTS

| | | | |
|---|---|---|---|
| 5,584,314 A | 12/1996 | Bron | |
| 6,871,740 B1* | 3/2005 | Cao | 206/364 |
| 7,763,142 B2* | 7/2010 | Watson | 156/293 |
| 2003/0135147 A1* | 7/2003 | Rosenberg et al. | 604/8 |
| 2006/0235439 A1 | 10/2006 | Molitor et al. | |

OTHER PUBLICATIONS

International Search Report issued Nov. 5, 2008 (published Mar. 19, 2009) during prosecution of International Application No. PCT/US08/75823.

Written Opinion issued Nov. 5, 2008 (published Mar. 19, 2009) during prosecution of International Application No. PCT/US08/75823.

* cited by examiner

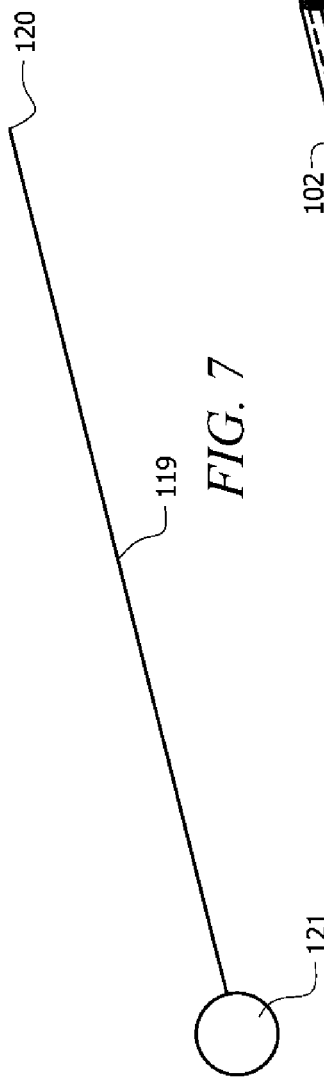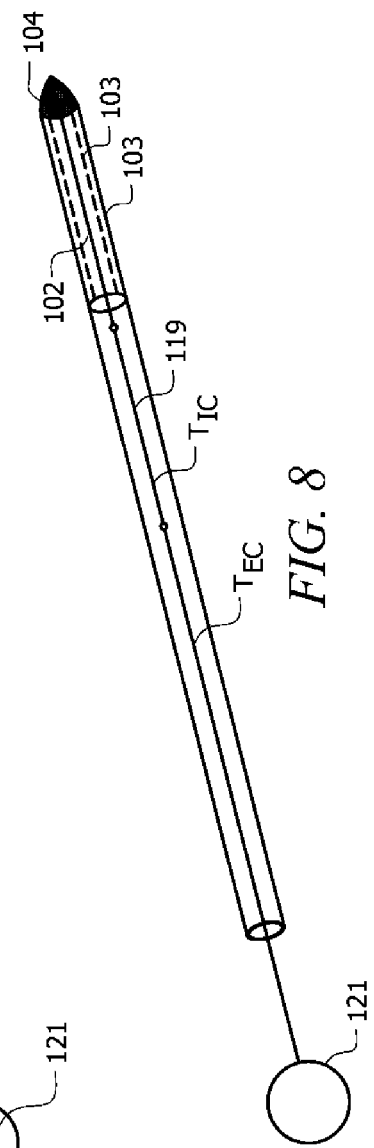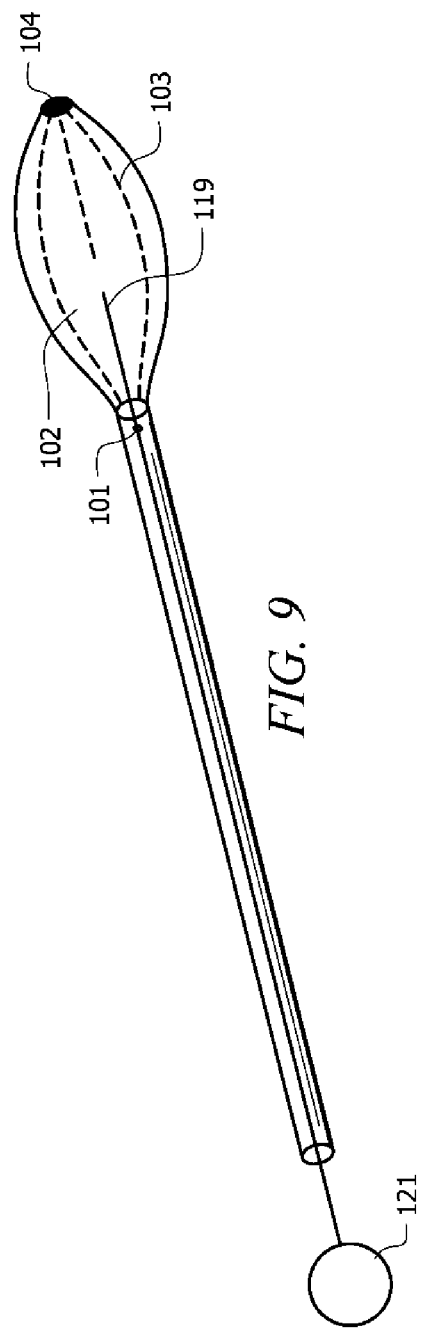

ANTI-CLOGGING VENTRICULAR CATHETER FOR CEREBROSPINAL FLUID DRAINAGE

CROSS-REFERENCE TO RELATED APPLICATIONS

The present invention claims priority to U.S. Provisional Patent Application Ser. No. 60/971,060, filed Sep. 10, 2007, which is incorporated by reference herein in its entirety.

TECHNICAL FIELD

The present invention relates to a particular ventricular catheter, including an anti-clogging ventricular catheter for a fluid, in particular for a cerebrospinal fluid (CSF) shunt, for example, used in the treatment of hydrocephalus.

BACKGROUND OF THE INVENTION

The CSF is produced by the choroid plexus that is located within the encephalic ventricles. Normal CSF production rate in an adult is 20 ml/hour (or 500 ml/day). The total CSF volume in an adult is 120 to 150 ml. Hence, in normal circumstances CSF is recycled over three times each day. CSF comprises of water (99%), proteins (<0.4 g/l), glucose (0.5 g/l), and chloride (115 mEq/l). Intracranial pressure (ICP) is measured in millimeters of mercury (mmHg) and, at rest, is normally less than 10-15 mmHg.

The ventricular system is a set of structures in the brain continuous with the central canal of the spinal cord. There are four cerebral ventricles: the paired lateral ventricles, and midline the third and fourth ventricles. The lateral ventricles both communicate via the interventricular foramina of Monro with the third ventricle, found centrally within the diencephalon. The third ventricle communicates via the cerebral aqueduct of Sylvius, located within the midbrain, with the fourth ventricle. The three foramina (foramen of Magendie and Lushka's foramina) open to the subarachnoid space. Each ventricle contains a choroid plexus that produces cerebrospinal fluid (CSF) used to bathe, cushion, protect, nourish and cleanse the brain and spinal cord within their bony confines.

CSF flows from the lateral ventricles via the foramina of Monro into the third ventricle, and then the fourth ventricle via the cerebral aqueduct in the brainstem. From there it can pass into the central canal of the spinal cord or into the cisterns of the subarachnoid space via three small foramina: the central foramen of Magendie and the two lateral foramina of Luschka. The fluid then flows around the superior sagittal sinus to be reabsorbed via the arachnoid villi into the venous system. CSF within the spinal cord can flow all the way down to the lumbar cistern at the end of the cord around the cauda equina where lumbar punctures are performed. Hydrocephalus occurs when the fluid cannot flow freely throughout the ventricles and the central nervous system due to various forms of blockage. Except in very rare cases, it is a life-long condition that can only be controlled, not cured, through surgical intervention.

Hydrocephalus

In the physiopathological definition of hydrocephalus, it is an active distension of the ventricular system of the brain resulting from inadequate passage of cerebrospinal fluid from its point of production within the cerebral ventricles to its point of absorption into the systemic circulation.

Causes:

There are two main types of hydrocephalus: congenital or acquired. The former means that the problem existed at birth, although it may not noticeably manifest itself until later in life, perhaps even adulthood. The latter means that the root cause of the hydrocephalus, whether it is head trauma, tumor or infection, occurred after birth.

Aqueductal obstruction, or stenosis, is the most common cause of congenital hydrocephalus. The cerebral aqueduct, which conducts CSF from the third to the fourth ventricle, is blocked due to defect, inflammation, tumor or hemorrhage. This forces CSF fluid to back up, thereby causing hydrocephalus.

Neural tube defects occur when the surrounding and supporting structure of the spinal cord, not the spinal cord itself, is defective or not fully developed. This malformation can create a blockage in the opening at the base of the skull, which in turn retards the flow of CSF from the fourth ventricle.

Intra-ventricular hemorrhage occurs most frequently in premature babies whose blood vessels in the brain have not been able to fully develop. Because of this weakness, the vessels can burst, thereby allowing the blood to block or scar the ventricles of the CSF pathways.

Meningitis, whether viral or bacterial in origin, causes inflammation of the membranes surrounding the brain and spinal cord. Scarring of these membranes may restrict the flow of CSF and lead to the onset of hydrocephalus.

In cases where head trauma occurs, blood from ruptured vessels may lead to inflammation and scarring of the brain membranes, or can even block the absorption of CSF into tissue. If these CSF flow restrictions occur, hydrocephalus develops.

Tumors may grow in the brain and compress areas of the ventricular system, or block the CSF pathways thereby restricting the flow of CSF and leading to the onset of hydrocephalus.

Arachnoid Cysts, or cysts made up of CSF-filled arachnoid membrane, may block the CSF pathways and bring on hydrocephalus. This condition is congenital and may occur anywhere in the brain.

In instances of Dandy-Walker Syndrome, a congenital defect, the fourth ventricle is enlarged and its outlets become obstructed. Because the flow of CSF throughout the brain is obstructed, hydrocephalus develops.

Mechanism and Symptoms:

Acute Hydrocephalus: Obstructive, or non-communicating, hydrocephalus occurs when the CSF does not flow properly between or out of the brain ventricles because of an obstruction, such as from a malformation or tumor. Symptoms of increased intracranial pressure may include headaches, vomiting, nausea, papilledema, sleepiness, or coma. Elevated intracranial pressure may result in uncal and/or cerebellar tonsil herniation, with resulting life threatening brain stem compression Chronic hydrocephalus: Non-obstructive, or communicating, hydrocephalus occurs when the CSF flows out of the brain ventricles and into the spinal canal, but it is not reabsorbed normally by the tissue surrounding the brain and spinal cord. Normal Pressure Hydrocephalus (NPH) is characterized by a triad of symptoms (Hakim triad) of gait instability, urinary incontinence and dementia is a relatively typical manifestation of the distinct entity normal pressure hydrocephalus (NPH).

Diagnosis:

Magnetic Resonance Imaging (MRI) is a non-invasive diagnostic tool that uses radio signals and a magnet to form computer images of the brain, its ventricular system and coverings, and pathological lesions.

Computerized Tomography (CT Scan) is a technique in which tiny beams of x-ray outline the skull, brain, ventricles, and subarachnoid space. In addition to visualizing the size and shape of the ventricles, abnormalities such as tumors, cysts, and other pathology can also be seen.

Controlled Lumbar Drainage is a technique used to externally drain CSF over a period of several days. The test is used to determine if a patient with NPH will improve with shunt placement.

Cisternography is a test requiring injection of a small amount of radioactive material into the CSF. This test differentiates communicating from obstructive hydrocephalus, and determines CSF flow.

Neuropsychological Tests are a series of questions and answers used to determine if there is decrease in brain functioning due to hydrocephalus.

Treatment: CSF Shunting

A shunt is a mechanical system that comprises a proximal catheter placed into a lateral ventricle; a valve for regulating the differential pressure gradient; and a distal catheter. In specific embodiments, the distal catheter is tunneled subcutaneously down and can be directed either into the peritoneal cavity (ventriculo-peritoneal shunt; VPS) or the right atrium of the heart (ventriculo-atrial shunt; VAS).

A Ventriculo-Peritoneal Shunt (VPS) diverts the CSF from the ventricles in the brain to the peritoneal cavity in the abdomen where the fluid is reabsorbed: the distal (or peritoneal) catheter runs from the valve down to the peritoneal cavity.

A Ventriculo-Atrial Shunt (VAS) diverts CSF from the ventricles of the brain into the right atrium of the heart. The distal (or atrial) catheter is placed into a vein in the neck and then carefully advanced into the right atrium of the heart, where the CSF is reabsorbed into the bloodstream.

Complications:

Complications may occur with shunt systems, including mechanical failure, infections, obstructions, and in some cases complications can lead to other problems such as overdraining or underdraining.

The cure of the obstruction and the repair of the system requires surgery which is not without risks. Revision surgery on patients with blocked shunts is occasionally complicated by serious secondary ventricular or intraparenchymal haemorrhage. The bleeding is caused when the choroid plexus is torn by the tip of the catheter as it is withdrawn.

Infections and anaesthetic complications may also occur.

One of the most common complications with shunts is shunt obstruction. Although obstruction or clogging may take place at any point along the shunt, the ventricular end is the most likely involved due to its small apertures. The ventricular tip of known shunts is punched with a series of holes and/or slots in the side of a silicone tubing piece. The CSF flows through these apertures into the lumen of the tubing. When the choroid plexus (which are the CSF secreting structures) or cellular debris (red cells and tumor cells, for example), or other brain tissues, for example, grow into the holes and invade the lumen of the catheter, the shunt is obstructed and surgery is needed to replace the ventricular catheter or attempt to clear its tip of this tissue.

The removal of the obstruction requires surgery that is not without risks. Revision surgery on patients with blocked shunts is occasionally complicated by serious secondary ventricular or intraparenchymal hemorrhage. The bleeding is caused when the choroid plexus is torn by the tip of the catheter as it is withdrawn. Infections and anaesthetic complications may also occur.

A high protein concentration in the CSF can also clog the shunt. It is known that a protein concentration higher than 4 g/l will clog up most of shunt valves.

U.S. Pat. No. 5,531,673 discloses a tubular ventricular catheter having an improved distal open end that reduces the tearing of any choroid plexus or other brain tissue that might grow into the lumen of the catheter. This catheter is also equipped with an electrical signal generator intended to prevent growth of tissue into the lumen. However, this ventricular catheter does not prevent the system downstream, and especially the valve, from clogging by a high protein concentration (hyperproteinorrachy).

In U.S. Patent Publication No. 2006/0235439, it is suggested that the majority of shunt malfunctions result from the obstruction of the distal catheter tip by accumulating particulate matter such as fat or proteinaceous debris. Thus, the proposed implantable device disclosed therein aims at maintaining the patency of the CSF shunt at its distal end (outlet) using mechanical energy to "scrub" the catheter lumen of particulate debris. This is accomplished by housing a source of mechanical energy that induces waveform in the CSF flowing through the peritoneal catheter.

U.S. Pat. No. 5,584,314 discloses a self-cleaning inlet head operable in both draining and back-flushing modes, using a slidable piston, intended to initiate a mechanical shearing action and loosening any occluding matter in the aperture. The mechanical action is followed by an hydraulic flushing action that can permit flushing some proteinaceous debris but certainly not clearing some tissue invasion.

There is therefore a need for a new designed ventricular catheter tip capable of preventing obstruction from tissue invasion but also clogging from protein precipitation or flocculation along the downstream shunt system.

BRIEF SUMMARY OF THE INVENTION

In accordance with a first aspect, a novel ventricular catheter is provided to reduce CSF shunt obstruction. In accordance with another aspect, a ventricular catheter is provided without openings along its wall to prevent clogging by ingrowth tissue or suctioned tissue. In accordance with another aspect, a ventricular catheter is provided with a tip having a membrane.

This membrane can be permeable or semi-permeable allowing certain molecules (for example, $H_2O$) or ions (electrolytes) to pass through it by diffusion but opposes to macromolecules (proteins), This membrane can be, for example, an expandable preshaped membrane, or not expandable.

The use of a membrane allows the CSF to flow through the membrane, but neither tissue (choroid plexus, blood cells, tumor cells, suctioned ependymal tissue, for example) nor proteins can break through the membrane and clog the shunt system, in particular embodiments.

Therefore, in accordance with one embodiment of the present invention, there is provided a ventricular catheter for allowing the flow of CSF from the cerebral ventricles, wherein the catheter has proximal and distal ends, the proximal end being adapted to connect to a valve while the distal end is positioned within the ventricular cavity, then expanded after having pushed out of its introducer. Once expanded, the semi-permeable membrane allows the CSF to flow through the proximal end of the shunt tubing but first prevent any tissue or cells from invading its lumen; it also prevents macromolecules such as proteins from entering within the shunt system, in specific embodiments.

Further in accordance with the present invention, in some embodiments there are provided exemplary methods for positioning the ventricular catheter depending on the use of either an introducer or a stylet, wherein the method comprises the steps of: (a) puncturing the cortex with the introducer or (a') puncturing the cortex with the ventricular catheter straightened by the stylet, (b) sliding out the introducer or (b') the stylet to allow the distal end of the ventricular to reach the ventricular cavity, (c) connecting the proximal end of the ventricular catheter to the valve.

Thus, in some embodiments of the invention, there is a ventricular catheter comprising a tube with an expandable membrane at one end. In specific embodiments, the membrane is semi-permeable. In further specific embodiments, the expandable membrane further comprises flexible ribs that help the expandable membrane hold a shape.

In specific cases, methods and/or compositions of the present invention are employed for a subject in need thereof, including in utero, an infant, an adolescent, or an adult, including in the elderly. The subject may be an individual with a medical condition that warranted use of the invention or the subject may be an individual that experienced trauma, for example.

In one embodiment of the invention, there is a ventricular catheter comprising a tube with a membrane at one end of the tube. In specific embodiments of the invention, the membrane is semi-permeable or permeable. In other specific embodiments, the membrane is expandable or non-expandable. In further aspects, the membrane is at least partially stretched by two or more flexible ribs. The tube is comprised of latex, silicone, or Teflon, in certain embodiments.

In specific embodiments, the semi-permeable membrane is comprised of polyacrylate, polyvinylidene, polyvinyl chloride copolymer, polyurethane, polystyrene, polyamide, cellulose acetate, cellulose nitrate, polysulfone, polyphosphazene, polyacrylonitrile, poly(acrylonitrile/covinyl chloride), or PTFE.

In a specific case, the catheter is housed in or with a device for implanting the catheter in a subject. In a specific embodiment, the device is cylindrical. In a specific embodiment, the device at least partially encases the catheter. In certain aspects, the device comprises one end that is slotted. In a particular aspect, the device is a stylet. The device is comprised of metal or plastic, in particular aspects.

In one embodiment of the invention, there is a kit for diverting cerebrospinal fluid from brain ventricle of a subject that comprises the ventricular catheter of the invention. In specific embodiments, the kit further comprises a device for implanting the catheter in a subject.

In another embodiment, there is a method of diverting cerebrospinal fluid from brain ventricle of a subject, comprising providing the ventricular catheter of the invention to the subject, including to a subject having hydrocephalus, for example. In a specific embodiment, the providing step comprises providing the catheter to the brain of the subject, wherein the catheter is enclosed in a device that keeps the membrane in a deflated shape; and removing the device. In a specific embodiment, the providing step comprises providing the catheter to the brain of the subject, wherein a stylet is positioned within the catheter and said catheter punctures the cortex.

From the foregoing disclosure and the following more detailed description of various preferred embodiments, it will be apparent to those skilled in the art that the present invention provides a significant advance in the technology and art of ventricular catheters. Particularly significant in this regard is the potential the invention affords for providing a high quality, low cost ventricular catheter adapted for specialized design constraints. Additional features and advantages of various preferred embodiments will be better understood in view of the detailed description provided below.

Other and further objects, features, and advantages would be apparent and eventually more readily understood by reading the following specification and by reference to the accompanying drawings forming a part thereof, or any examples of the presently preferred embodiments of the invention given for the purpose of the disclosure.

BRIEF DESCRIPTION OF THE DRAWINGS

FIG. 7 is a plan view of a stylet.

FIG. 8 is a schematic cross-sectional plan view of a straightened ventricular catheter when a stylet has been introduced.

FIG. 9 is a schematic cross-sectional plan view of a ventricular catheter and its completely expanded tip when the stylet has been slid out.

Figure 1:
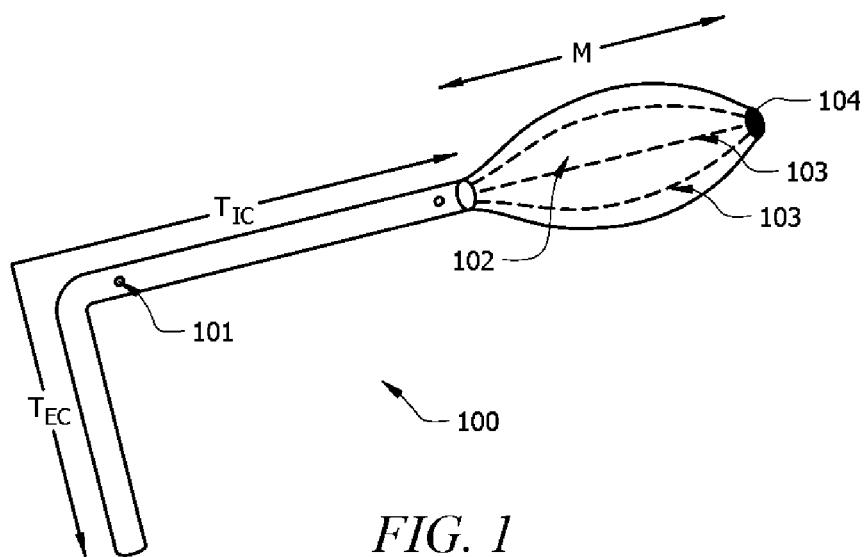
FIG. 1 is a schematic perspective view of a right angle ventricular catheter and its distal tip with the membrane expanded by memory pre-shaped flexible ribs at the rest position (unconstrained) in accordance with a preferred embodiment.

It should be understood that the appended drawings are not necessarily to scale, presenting a somewhat simplified representation of various preferred features illustrative of the basic principles of the invention. The specific design features of the ventricular catheter as disclosed here will be determined in part by the particular intended application and use environment. Certain features of the illustrated embodiments have been enlarged or distorted relative to others to help visualization and clear understanding. In particular, thin features may be thickened, for example, for clarity of illustration. All references to direction and position, unless otherwise indicated, refer to the orientation illustrated in the drawings.

DETAILED DESCRIPTION OF CERTAIN EMBODIMENTS OF THE INVENTION

It will be apparent to those skilled in the art, that is, to those who have knowledge or experience in this area of technology, that many uses and design variations are possible for the ventricular catheter disclosed here. The following detailed discussion of various alternative and preferred features and embodiments will illustrate the general principles of the invention with reference to a ventricular catheter suitable for use on patients with high CSF pressures. Other embodiments suitable for other applications will be apparent to those skilled in the art given the benefit of this disclosure.

It will be readily apparent to one skilled in the art that various embodiments and modifications may be made in the invention disclosed herein without departing from the scope and spirit of the invention.

Unless defined otherwise, technical and scientific terms used herein have the same meaning as commonly understood by one of ordinary skill in the art to which this invention belongs. For purposes of the present invention, the following terms are defined below.

As used herein, the use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

The term "catheter" as used herein refers to a hollow flexible tube made of but not limited to silicone, latex, Teflon or plastic for insertion into a body cavity (cerebral ventricles), to allow the passage of fluids (CSF).

The term "expandable" as used herein refers to a material capable of enlargement, e.g. able to increase, dilate, distend or stretch by lengthening and/or widening its size, volume, and/or surface. This feature is useful because in narrowing the diameter of the catheter (narrowed configuration), it makes the trans-cortical ventricular puncture possible, and then, in deploying the membrane (expanded configuration) within the ventricular cavity, it allows an adequate flow/unit surface area.

The term "hydrocephalus" as used herein refers to a pathological condition in which there is an excessive accumulation of cerebrospinal fluid (CSF) within the head caused by a disturbance of its formation, flow, and/or absorption that leads to the enlargement of one or more of the encephalic ventricular cavities. Hydrocephalus is defined as an active distension of the ventricular system of the brain resulting from inadequate passage of cerebrospinal fluid from its point of production within the cerebral ventricles to its point of absorption into the systemic circulation. In particular cases, it requires a surgical procedure intended to divert the excess CSF and may be accomplished by the surgical placement of a shunt.

The term "non-expandable" as used herein refers to a material unable to increase its size, volume, surface or change its shape. It has a fixed, predetermined size and shape.

The term "shunt" as used herein refers to a mechanical system that comprises a proximal catheter placed into a lateral ventricle; a valve for regulating the differential pressure gradient; and a distal catheter. In specific embodiments, the distal catheter is tunneled subcutaneously down and can be directed either into the peritoneal cavity (ventriculo-peritoneal shunt; VPS) or the right atrium of the heart (ventriculo-atrial shunt; VAS).

The term "Ventriculo-Peritoneal Shunt (VPS)" as used herein diverts the CSF from the ventricles in the brain to the peritoneal cavity in the abdomen where the fluid is reabsorbed: the distal (or peritoneal) catheter runs from the valve down to the peritoneal cavity.

The term "Ventriculo-Atrial Shunt (VAS)" as used herein diverts CSF from the ventricles of the brain into the right atrium of the heart. The distal (or atrial) catheter is placed into a vein in the neck and then carefully advanced into the right atrium of the heart, where the CSF is reabsorbed into the bloodstream.

The term "stylet" as used herein is defined as a wire, filament, thread, cord, strand, or fiber that can run through the length of a catheter, for example to make it rigid and/or maneuverable.

I. General Embodiments of the Invention

The present invention concerns a novel ventricular catheter designed to reduce CSF shunt obstruction. Such a ventricular catheter is provided with a tip having a membrane without openings along its wall to prevent clogging by in-growth of tissue or suctioned tissue. The present invention provides a novel and elegant improvement over known ventricular catheters in the art, because it reduces the clogging of shunts by tissue and/or proteins, for example, which impair the capacity of the shunt to divert the CSF. The ventricular catheter is capable of preventing or reducing clogging because the shunt utilizes a membrane that allows passage of certain materials but prevents ingrowth of tissue, and the ventricular catheters of the invention also lack any openings along its intra-cerebral intra-ventricular length in which tissue may be allowed to grow, for example.

Referring now to the drawings, FIG. 1 shows an exemplary ventricular catheter 100 comprising a right-angled silicone tube T and an expandable balloon-like semi-permeable membrane M. The ventricular catheter 100 is expanded at a rest position. The right-angled part T is a silicone tube intended to connect to a valve and to open up to a volume enclosed in an expandable semi-permeable membrane M. T is a (optionally) clear silicone tubing with an intra-cerebral leg $T_{ic}$ and an extra-cerebral leg $T_{ec}$. $T_{ic}$ has X-ray detectable markings (101) and the lengths of the intra-cerebral portion of the ventricular catheter ($T_{ic}$+M) are from 3 to 11 cm.

The length of the extra-cerebral portion of the ventricular catheter ($T_{ec}$) may be of any suitable length, although in certain embodiments the length is in a range of 10 to 25 cm when used with an introducer (106): It may be cut at the adequate length to connect to the valve. The length of the extra-cerebral portion of the ventricular catheter ($T_{ec}$) may be of any suitable length, although in certain embodiments the length is in a range of 2 to 10 cm when used with a stylet (119). M comprises a semi-permeable membrane (102). Its balloon-like shape is due to several memory pre-shaped flexible ribs (103) that keep the membrane unfolded at the rest position. These ribs are bent from the end of the intra-cerebral leg $T_{ic}$ to the apex (104) of the balloon. The unfolded membrane may have different shapes (spherical, ovoid, globular, rotund, oblong, elliptical, cylindrical helix, coil-shaped as a "serpentine"), sizes, and composition in order to have an adequate flow/unit surface area for the proposed geometry. The membrane comprises a resilient, bio-compatible, non-toxic, and non-resorbable material, in particular embodiments.

The exemplary semi-permeable membrane (102) allows certain molecules (for example, $H_2O$) or ions (electrolytes) to pass through it by diffusion but opposes to macro-molecules (proteins), in particular cases. The rate of passage depends on the pressure on either side, e.g. the differential pressure gradient between the intra-cranial pressure (ICP) and the selected pressure of the valve. When the ICP is superior to the selected pressure of the valve, the CSF flows through the membrane, but neither tissue (choroid plexus, blood cells, tumor cells, ependymal tissue suctioned) nor proteins can break through the membrane, in certain aspects.

Figure 2:
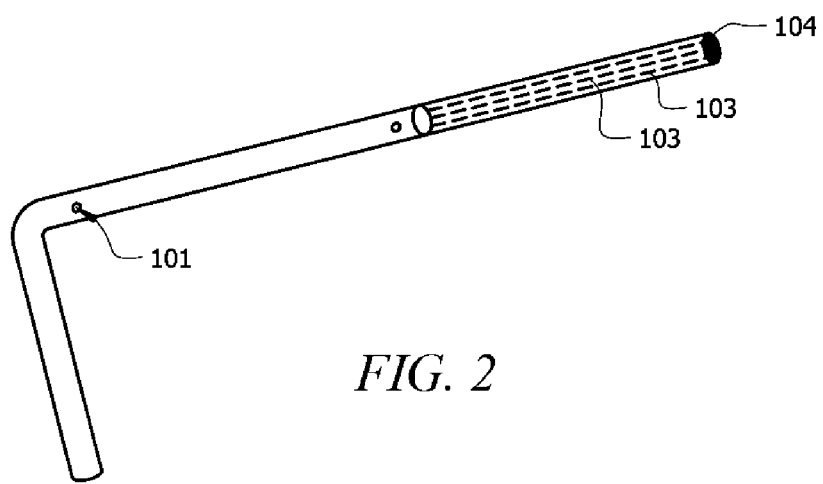
FIG. 2 is a schematic perspective view of a right angle ventricular catheter showing its distal tip when the membrane is narrowed (under constraint of its case/introducer: not shown in this figure) in accordance with the present invention.

FIG. 2 shows the ventricular catheter when the memory pre-shaped flexible ribs are constrained (constraining device not shown) and the membrane is deflated.

This contractile property narrows the diameter of the catheter, therefore allows the catheter to be slid through a cylindrical case (106) and then positioned within the ventricle using a minimally invasive trans-cortical approach. In this constrained position, the outer diameter of the entire ventricular catheter does not exceed 6 mm.

Figure 3:
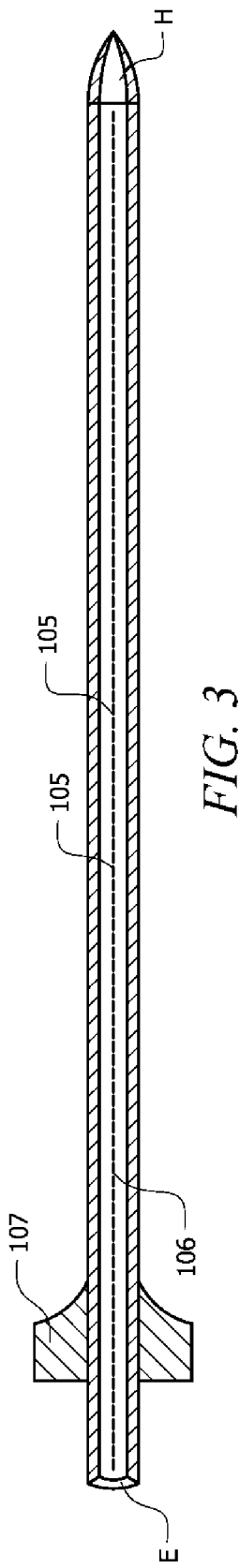
FIG. 3 is a schematic perspective view of the case/introducer.

FIG. 3 is a cross-sectional lateral view of an exemplary introducer (106). Its external end (E) is circular and intended to receive the ventricular catheter. Its internal end (I) is blunt to act as a canula for puncturing the cortex but is slotted so that it can first leave passage to the ventricular catheter and then, act as an open/close obturator to prevent excessive loss of CSF while puncturing the ventricle, in specific embodiments.

The introducer is sterile and disposable, in specific embodiments. In particular cases, it comprises a transparent plastic to allow seeing the progression of the ventricular catheter when inserted.

A centimetric scale is also shown along its wall, in specific cases. A handle (107) allows to securely hold the introducer after the ventricle's puncture and during the catheter insertion, in certain aspects. Its length is from 10 to 15 cm. Its inner diameter matches the outer diameter of the constrained ventricular catheter.

Figure 4:
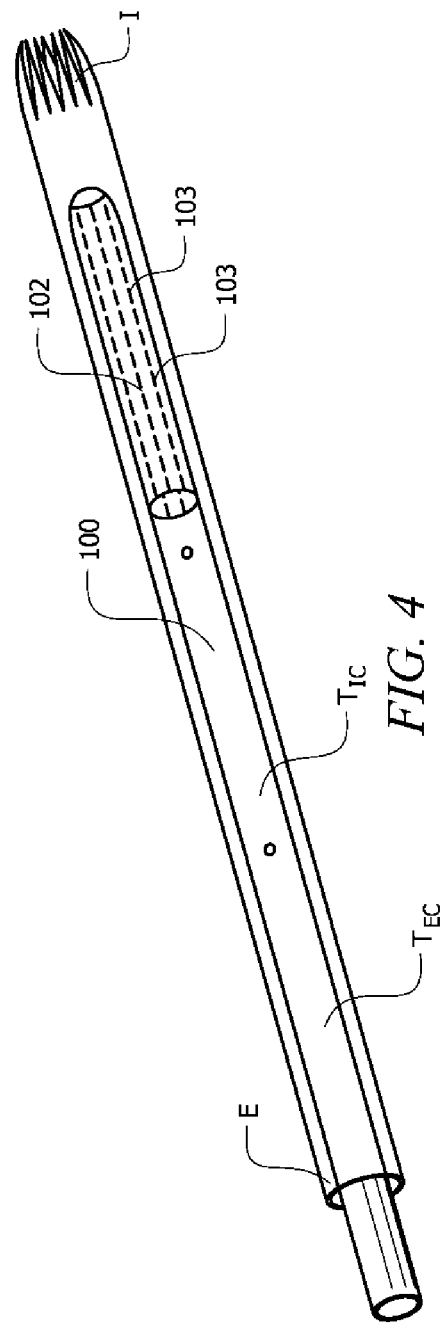
FIG. 4 is a schematic cross-sectional plan view of a straightened ventricular catheter within its introducer and the contracted, narrowed membrane.

FIG. 4 is a cross-sectional view of the first step of the ventricular catheter (100) insertion. The catheter (100) has been inserted through the external opening (E) of the introducer (106). The ribs (103) are constrained by the inner wall of the introducer (106) and the membrane (102) is folded. The junction between the intra-cerebral leg (Tic) and the extra-cerebral leg (Tec) of the flexible silicone-based tube (T) is straightened by the inner wall of the introducer (106). The internal end (I) of the introducer (106) is still closed, in this particular figure.

Figure 5:
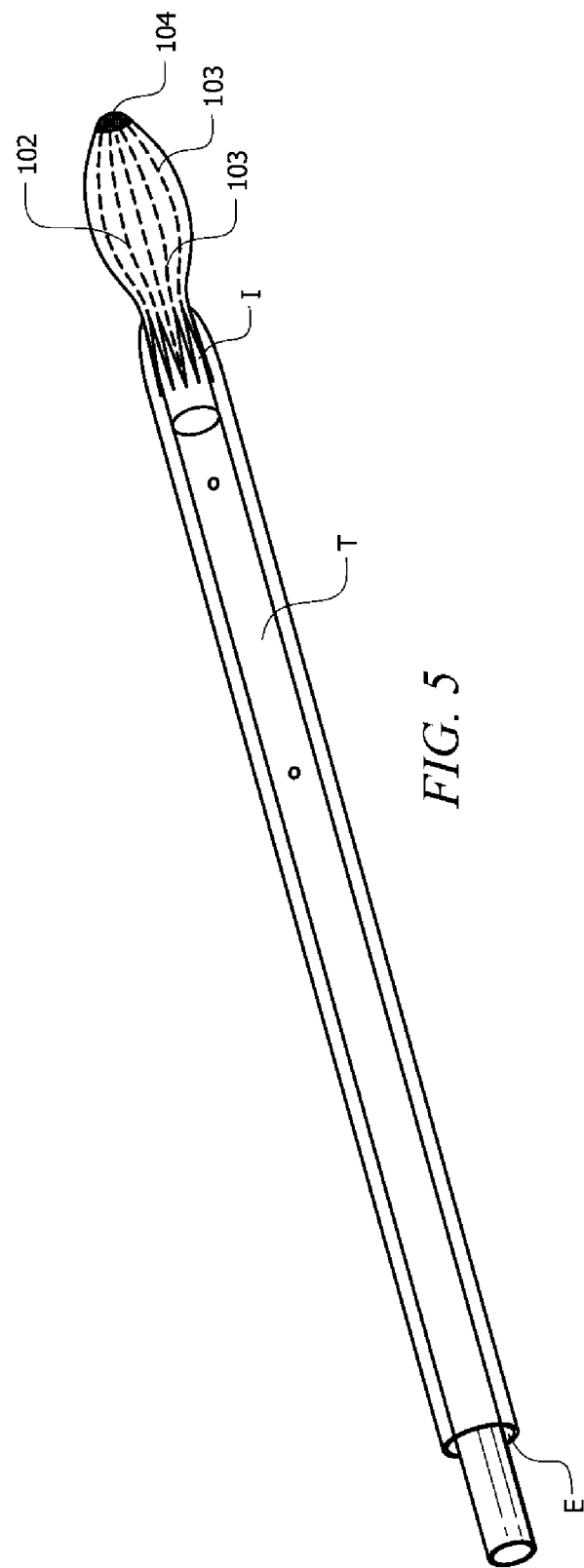
FIG. 5 is a schematic cross-sectional plan view of a straightened ventricular catheter and its partially expanded tip when the introducer is sliding out.

FIG. 5 shows an intermediate step of the ventricular catheter insertion. The introducer (106) is securely held while the ventricular catheter is gently pushed into the ventricular cavity. Its distal end (104) has spread out the slots of the internal end (I) of the introducer (106) which is then widely open and therefore allows the ventricular catheter (100) to pass through it. Once breaking into the ventricular cavity, the memory pre-shaped flexible ribs (103) spontaneously return to their pre-shaped conformation and therefore allow the membrane (102) to begin to deploy.

Figure 6:
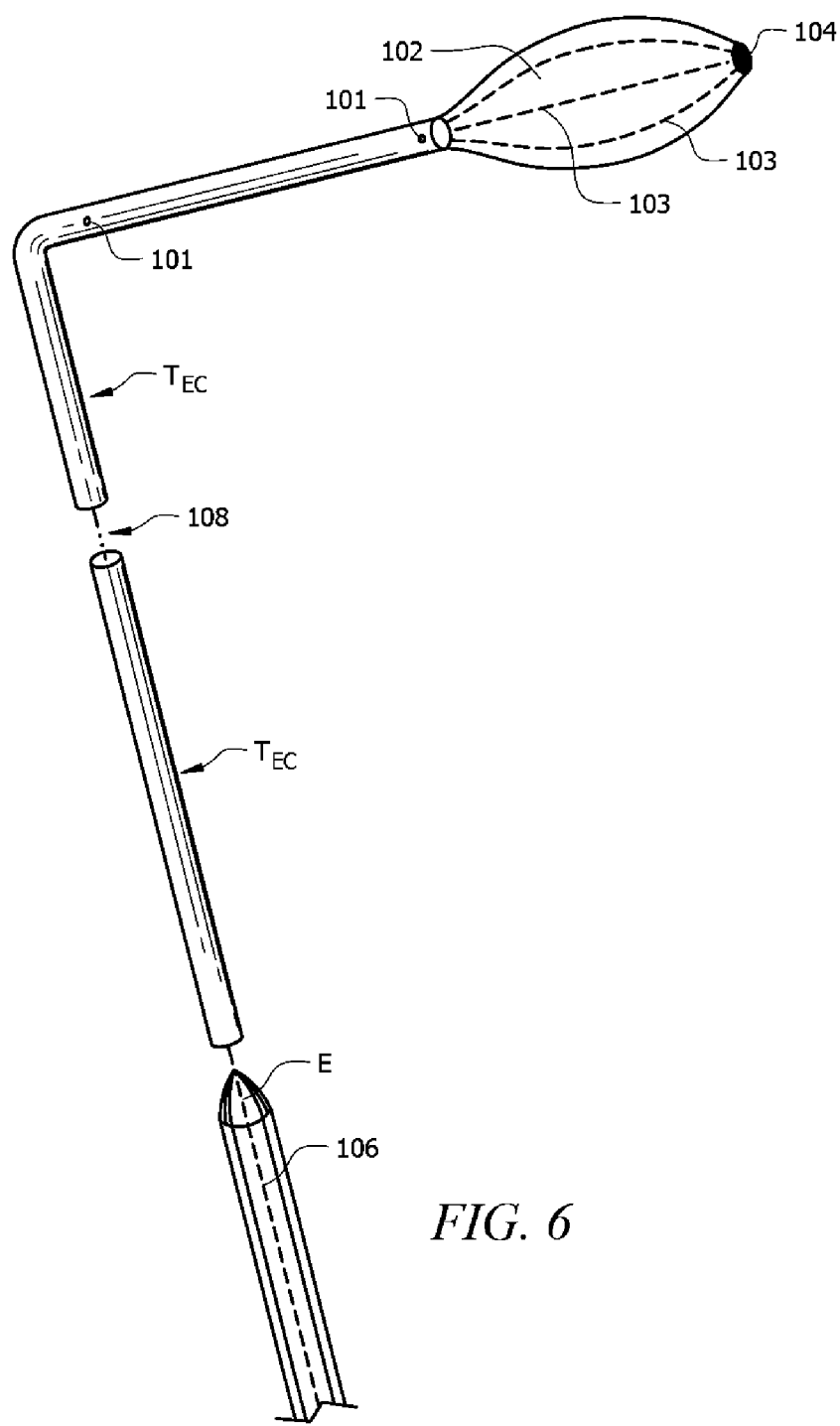
FIG. 6 is a schematic cross-sectional plan view of a ventricular catheter and its completely expanded tip when the introducer has been slid out.

FIG. 6 shows the last step of the ventricular catheter insertion. The introducer (106) is gently slid out backward so that the ventricular catheter (100) is released with the completely expanded semi-permeable membrane (105) within the ventricular cavity, the segment $T_{ic}$ adequately positioned into the brain parenchyma, the right angle outside the cranium, and the segment $T_{ec}$ cut (108) at the right length to connect to a valve after the complete removal of the introducer (106).

FIG. 7 shows an exemplary stylet, for example a sterile stainless steel stylet (119) of any suitable length e.g. from 5 to 20 cm. It is intended to permit the catheter insertion through the cortex. It is designed to be inserted within the lumen of the ventricular catheter in order first to straighten the angulated tube and then spread out the ribs (103) by leaning on the inner part of the ventricular catheter tip (104) and therefore fold the membrane (102). The stylet's proximal end (121) is shaped in such a way to widen its proximal end and ease its handle like a ring-shaped end for example.

FIG. 8 is a cross-sectional view of the ventricular catheter (100) set into its narrowed configuration for the trans-cortical ventricular puncture. The stylet (119) has straightened the angulated flexible silicone-based tube ($T_{ic}$ and $T_{ec}$) and squeezed the ribs (103) and folded the membrane (102) by leaning on the catheter tip (104).

FIG. 9 is a cross-sectional view of the ventricular catheter (100) at the removal of the stylet (119). The suppression of the pressure onto the tip (104) permits the memory pre-shaped flexible ribs (103) to expand and the semi-permeable membrane (102) to unfold.

Figure 10:
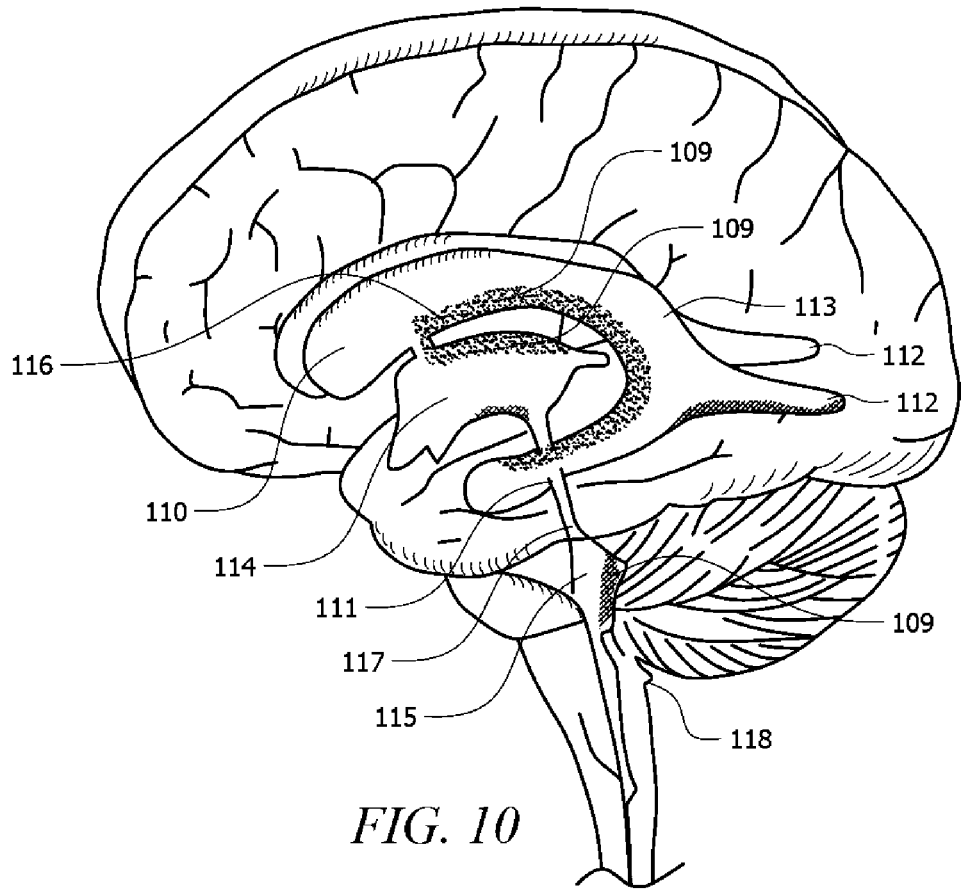
FIG. 10 is a perspective view of the encephalon and the ventricular system.

FIG. 10 is a perspective view of the encephalon and the ventricular system. There are four cerebral ventricles: the paired lateral ventricles, and midline the third (114) and fourth (115) ventricles. The two lateral ventricles, located within the cerebrum, are relatively large and C-shaped: frontal horn (110), temporal horn (111), occipital horn (112) that connects together at the ventricular junction (113). The lateral ventricles both communicate via the interventricular foramina of Monro (116) with the third ventricle (114), found centrally within the diencephalon. The third ventricle communicates via the cerebral aqueduct of Sylvius (117), located within the midbrain, with the fourth ventricle (115). The three foramina (foramen of Magendie (118) and Lushka's foramina) open to the subarachnoid space.

Figure 11:
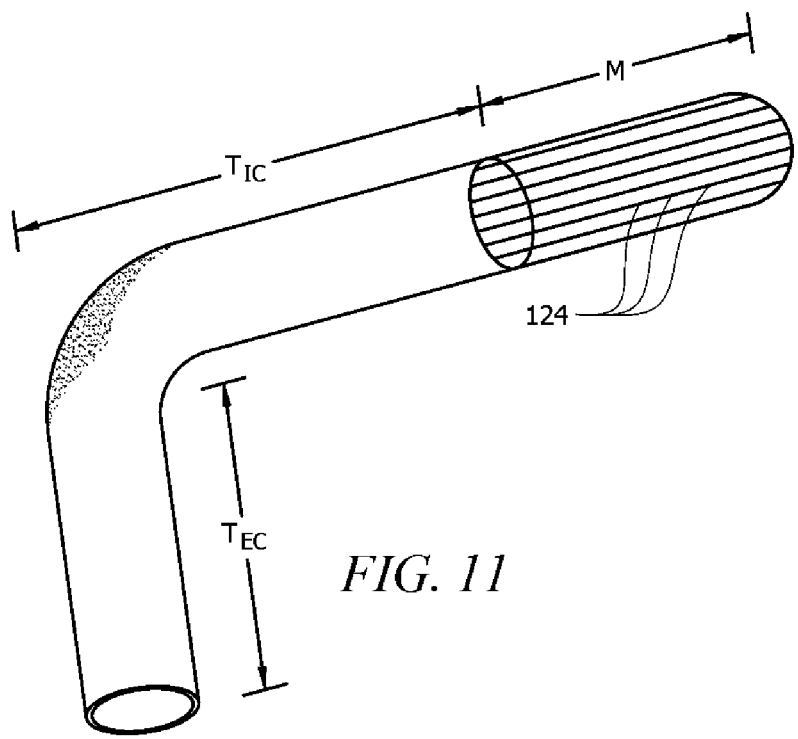
FIG. 11 is a schematic perspective view of a right angle ventricular catheter showing its distal tip with a non-expandable membrane using rigid ribs.

FIG. 11 is a schematic perspective view of a right angle ventricular catheter showing its distal tip with a non-expandable membrane stretched between rigid ribs. The diameter of both $T_{ic}$ and M portions is the same. The rigid ribs (124) act as a framework to tighten the membrane. It can be inserted within the ventricular cavity according to the classical current technique using a stylet.

Figure 12:
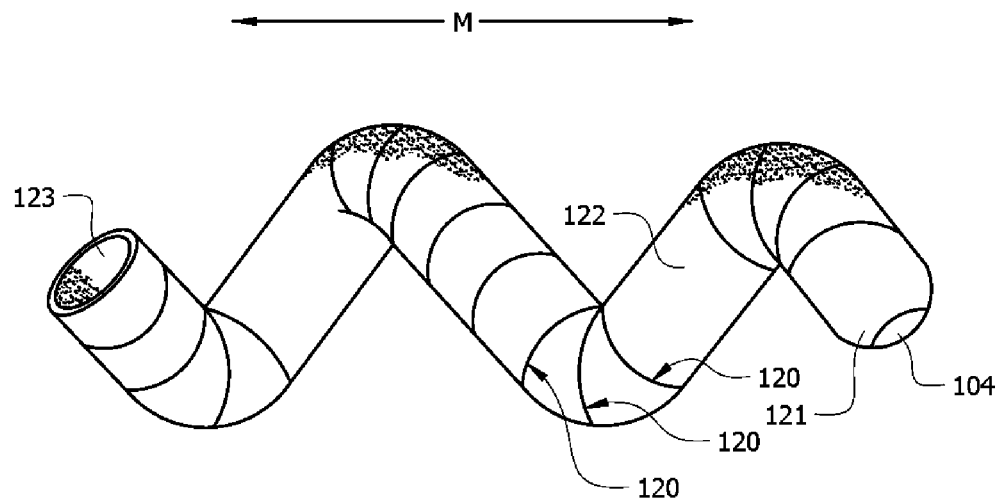
FIG. 12 is a perspective view of a coil-shaped (serpentine) membrane using a memory cylindrical helix shaped ribs.

FIG. 12 is a perspective view of a coil-shaped (serpentine) membrane (122) using a memory cylindrical helix shaped ribs (120). The proximal end (123) of the membrane portion M connects to the intra-cerebral leg $T_{ic}$ of the silicone tube T. The distal end (121) is reinforced and thickened at its apex to allow the stylet leaning on the inner part of the ventricular catheter tip (104).

Figure 13:
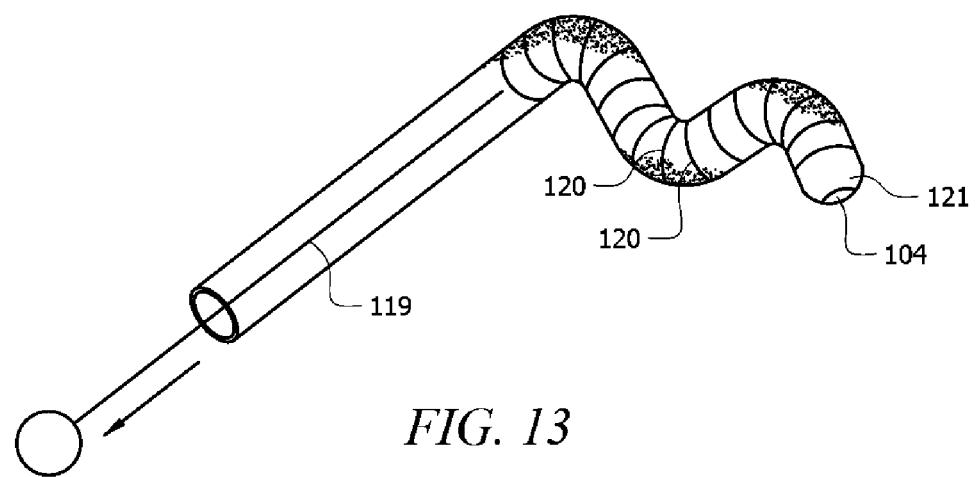
FIG. 13 is a schematic perspective view of a straightened coil-shaped ventricular catheter and its partially non-expandable tip when the stylet is pulled out.

FIG. 13 shows an intermediate step of the ventricular catheter insertion. After puncture of the ventricle, the distal end of the ventricular catheter is released within the ventricular cavity by gently pulling out the stylet. Due to the memory coil-shaped ribs, the distal end regains its cylindrical helix shape.

Figure 14:
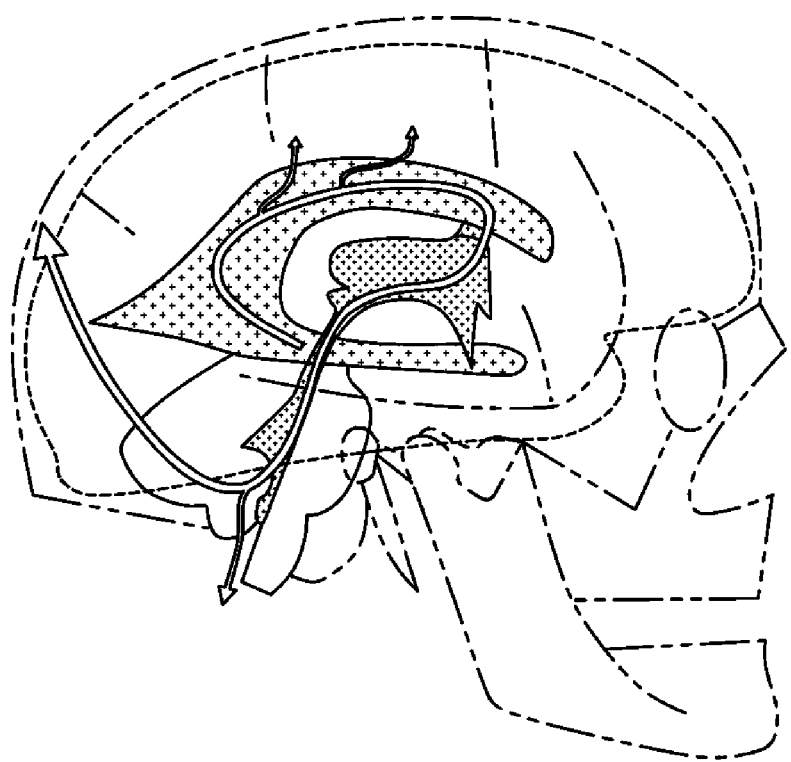
FIG. 14 is a schematic view of the CSF circulation

FIG. 14 shows the CSF circulation within the nervous central system: It is produced from the choroid plexus located within the ventricles and flows from the lateral ventricles via the foramina of Monro into the third ventricle, and then the fourth ventricle via the cerebral aqueduct in the brainstem. From there it can pass into the central canal of the spinal cord or into the cisterns of the subarachnoid space via three small foramina: the central foramen of Magendie and the two lateral foramina of Luschka. The fluid then flows around the superior sagittal sinus to be reabsorbed via the arachnoid villi into the venous system.

Figure 15:
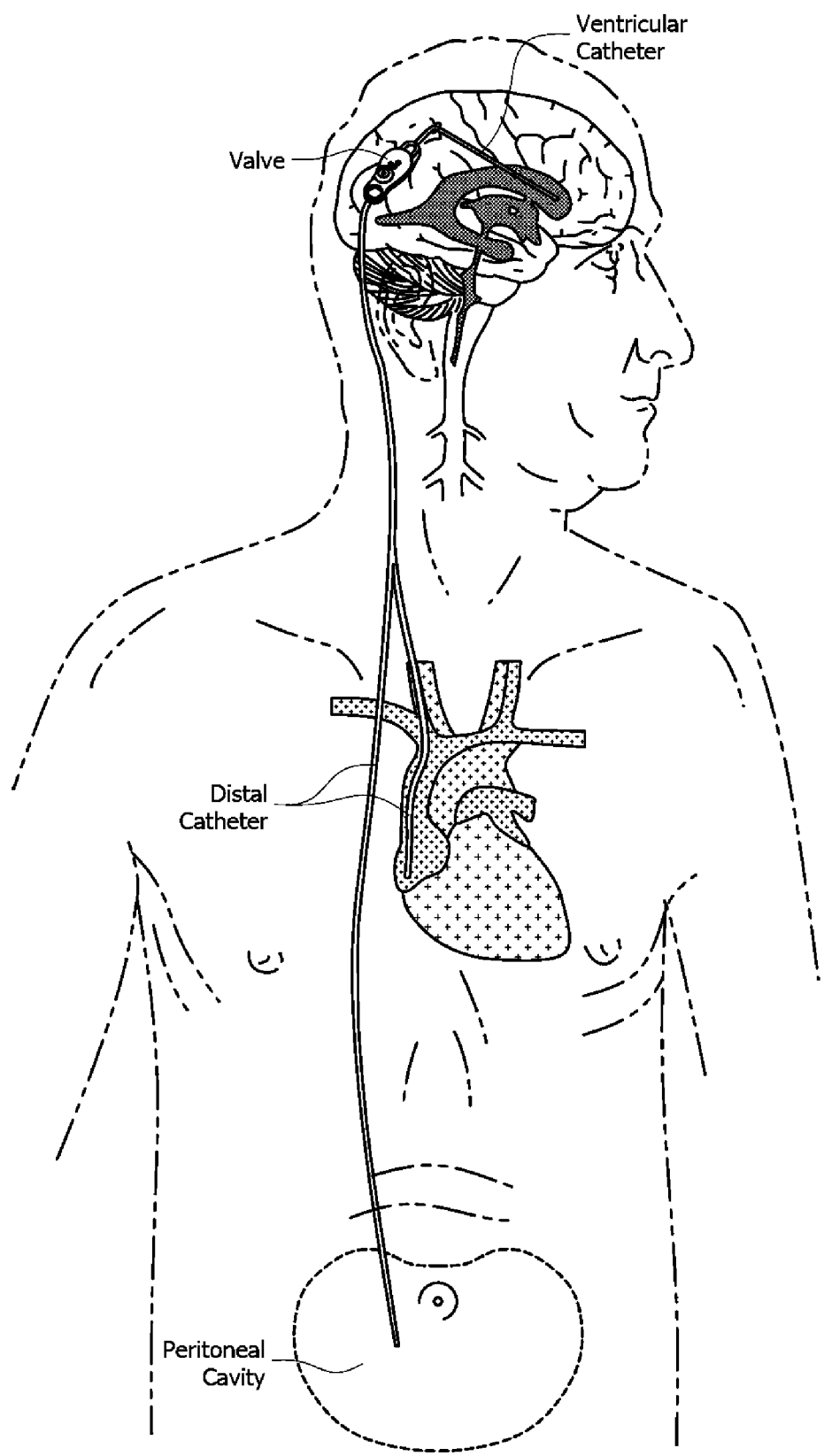
FIG. 15 shows a ventriculo-peritoneal shunt (VPS) as well as a ventriculo-atrial shunt (VAS)

FIG. 15 shows a ventriculo-peritoneal shunt (VPS) as well as a ventriculo-atrial shunt (VAS): Shunts are mechanical devices that include a proximal catheter placed into a lateral ventricle, a valve intended to regulate the differential pressure gradient, and a distal catheter. The distal catheter is inserted subcutaneously down and can be directed either into the peritoneal cavity (Ventriculo-Peritoneal Shunts or VPS) or the right atrium of the heart (Ventriculo-Atrial Shunts or VAS).

Figure 16:
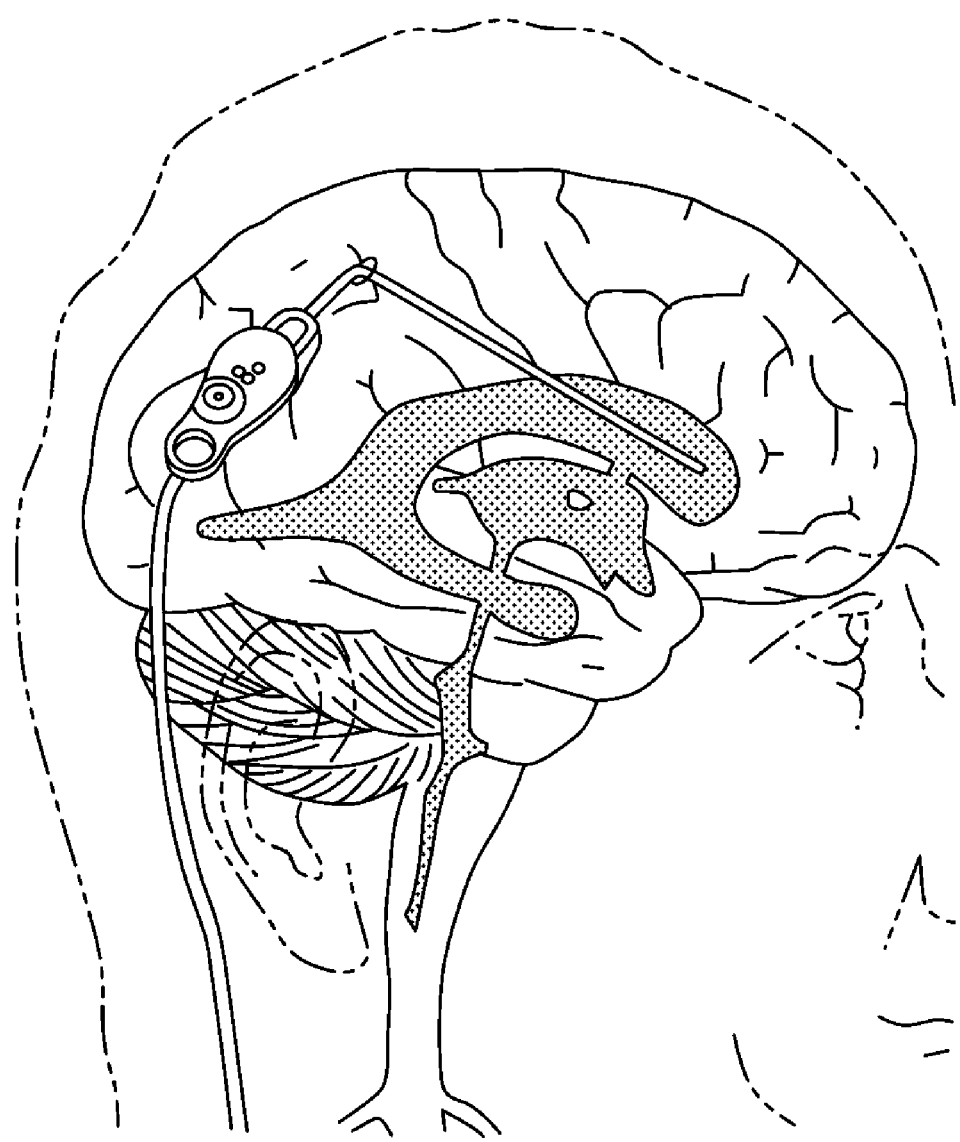
FIG. 16 is a close-up view of the ventricular catheter connected to the valve.

FIG. 16 is a close-up view of a ventricular catheter inserted through the right parieto-occipital region and connected to a valve.

A pair of exemplary methods for positioning the ventricular catheter is disclosed herein, depending on the use of either an introducer or a stylet.

In one embodiment, there is a method using an introducer: After drilling a burr hole in the right parieto-occipital region or in the right frontal region, the cortex of the brain is cauterized then punctured with the introducer, which is gently headed to the ventricular junction. The right positioning within the ventricle is demonstrated by the collection of CSF. The centimetric scale indicates the thickness of the cerebral parenchyma, and it allows one to choose the desired length of the ventricular catheter accordingly. Then, the ventricular catheter is introduced at the external opening of the introducer and slid in. Its progression is followed under control of the view through the transparent introducer. When the needed length of the ventricular length has been introduced, the introducer is gently slid out, which allows the distal end of the ventricular catheter to expand within the ventricle and the tube to return to its right angle configuration. Once the introducer is removed from the ventricular catheter, the external tube is cut at the right length to be adequately connected to the valve.

In another embodiment, there is an exemplary method using a stylet. After drilling a burr hole in the right parieto-occipital region or in the right frontal region, the cortex is cauterized and then punctured with the ventricular catheter straightened by the stylet. The right positioning within the ventricle is demonstrated by the collection of CSF at its external end. Then, the stylet is removed, which allows the distal end of the ventricular catheter to expand within the ventricle and the tube to return to its right angle configuration. The catheter is connected to the valve.

II. Membrane Embodiments of the Invention

In specific embodiments, the ventricular catheter is an improvement over those in the art, which are prone to having obstruction or clogging due to its small apertures. When the choroid plexus or cellular debris (for example, red cells, tumor cells, and so forth) or other brain tissue grows into the holes of the shunts used in the art and invade the lumen of the catheter, or when a high protein concentration in the CSF occurs, the ventricular catheter is obstructed and the shunt is no longer capable of diverting the CSF either to the peritoneum or the heart. In this case, surgery is needed to replace the ventricular catheter or attempt to clear its tip of this tissue.

A catheter is an extremely narrow piece of tubing used for drainage purposes.

"Proximal" refers to the catheter placed in the area to be drained (ventricular cavities of the brain), while "distal" refers to the catheter placed in the area accepting the CSF to be absorbed (peritoneum, or heart).

In the proximal catheter of the present invention, a ventricular catheter tip is capable of preventing obstruction from tissue invasion but also clogging from protein precipitation or flocculation along the downstream shunt system. This is made possible by using a ventricular tip designed without any openings and capable of filtering the CSF.

There are no openings along the length of the catheter. Without any openings, it makes the shunt obstruction by in-growth tissue or tissue invasion impossible. In specific embodiments, the catheter comprises a membrane at one end and an opening at the other end. In particular embodiments, the proximal catheter comprises a membrane and two or more ribs, including two, three, four, five, six, seven, eight, nine, ten, or more ribs.

A catheter is a flexible tube made of latex, silicone, or Teflon that can be inserted into the body creating a channel for the passage of fluid. The lengths of the intra-cerebral portion of the ventricular catheter ($T_{ic}$+M) are from 3 to 11 cm. The length of the extra-cerebral portion of the ventricular catheter ($T_{ec}$) varies between 2 cm and 25 cm. In catheters present in the art, the ventricular diameters are comprised between 3.1 mm (outer diameter or O.D) and 1.5 mm (inner diameter or I.D). The range of size of the present invention is comprised between 3 to 6 mm for the outer diameter, and 1 to 3 mm for the inner diameter.

A. Membrane

In certain aspects of the invention, the physical and/or chemical properties of the membrane allow the CSF to flow throw it according to the differential pressure gradient between the intra-cranial pressure (ICP) and the selected pressure of the valve.

The membrane comprises a resilient, bio-compatible, non-toxic, and non-resorbable material, in particular embodiments.

i. Expandable

In particular embodiments of the invention, the ventricular catheter comprises an end with an expandable(semi-permeable or permeable) membrane.

In specific embodiments, the membrane is a balloon-like (semi-permeable or permeable) membrane. The expandable feature is intended to increase the area of exchange between the CSF and the membrane, so that an adequate flow/unit surface can be achieved.

In certain aspects, a memory pre-shaped framework (flexible ribs) permits the expansion of the (semi-permeable or permeable) membrane when released within the ventricular cavity.

In certain aspects, the (semi-permeable or permeable) membrane is expanded to a spherical, elliptical, ovoid, globular, rotund, oblong, etc., shape. In specific cases, it is useful to have a shape that permits a large area of exchange compared to a spherical or elliptical shape.

In alternative embodiments (FIG. 12 and FIG. 13), the shape of the (semi-permeable or permeable) membrane may be "serpentine" (e.g. cylindrical helix, coil-shaped), in order to have an adequate flow/unit surface area for the proposed geometry. Memory pre-shaped flexible ribs permits the deployment of this coil-shaped end.

ii. Non-Expandable

In an alternative embodiment (FIG. 11), rigid ribs stretch a non-expandable (semi-permeable or permeable) membrane.

iii. Semi-Permeable

In particular cases, the membrane is semi-permeable, which allows certain molecules (water) or ions (electrolytes) to pass through it by diffusion but opposes macro-molecules (proteins), and it therefore acts as a filter making protein precipitation or flocculation impossible or at least reduced within the shunt system.

A semi-permeable membrane may be employed, examples of which include various polymers and polymer blends, including but not limited to, polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), PTFE, as well as derivatives, copolymers and mixtures of the foregoing, for example.

This semi-permeable membrane may be expandable or not expandable.

iv. Permeable

In particular cases, the main cause of obstruction comes from tissue invasion, and only a minor number of obstruction is caused from protein flocculation, precipitation or coagulation. Therefore, in particular aspects a simple permeable membrane is employed that allows at least some proteins to pass through. Such permeable membrane is permeable to ions, molecules, macro-molecules (proteins, for example) but hermetic to cells and tissues.

A simple permeable membrane may be employed: A good cell-filtration efficiency can be obtained with a 20 nm porous membranes, for example. This simple permeable membrane may be expandable or not expandable.

B. Ribs

1. Flexible Ribs

They are made of a memory non-metallic material (such as, but not limited to plastics, polymers or titanium) and used as a deployable framework once released out of the introducer or stylet within the ventricular cavities.

They allow the membrane (semi-permeable or permeable, expandable or non-expandable) to get the appropriate pre-determined shape, size, volume, and/or surface once released within the ventricular cavities.

Ultimately, they increase the area of exchange between the CSF and the membrane, so that an adequate flow/unit surface can be achieved.

In particular embodiments, the ventricular catheter is narrowed when the flexible ribs are constrained (into the introducer, or spread out by the stylet) and the membrane is folded making the trans-cortical puncture possible. Then, once released unconstrained within the ventricle, the ribs return to their pre-shaped configuration and unfold the permeable or semi-permeable membrane, in specific embodiments.

In specific embodiments of the invention, the ribs are comprised of memory pre-shaped bio-compatible plastic that is able to spontaneously and mechanically deploy the membrane once the distal tip has reached the ventricle cavity.

2 Rigid Ribs

In specific embodiments of the invention, the ribs are rigid in order to mechanically keep the membrane appropriately stretched within the ventricular cavity.

They stretch out the membrane between the distal opening of the intra-cerebral leg ($T_{ic}$) and the apex of the ventricular catheter tip (104).

C. Introducers

In specific embodiments, an introducer intended to straighten the ventricular catheter is provided. Its external end (E) is circular and intended to receive the ventricular catheter. Its internal end (I) is blunt to act as a canula for puncturing the cortex but is slotted so that it can first leave passage to the ventricular catheter and then, act as an open/close obturator to prevent excessive loss of CSF while puncturing the ventricle, in specific embodiments.

The introducer is sterile and disposable, in specific embodiments. In particular cases, it comprises a transparent plastic to allow seeing the progression of the ventricular catheter when inserted.

A centimetric scale is also shown along its wall, in specific cases. A handle (107) allows to securely hold the introducer after the ventricle's puncture and during the catheter insertion, in certain aspects. Its length is from 10 to 15 cm. Its inner diameter matches the outer diameter of the constrained ventricular catheter.

D. Stylets

In specific embodiments, a stylet intended to straighten the ventricular catheter is provided, for example a sterile stainless steel stylet (119) of any suitable length e.g. from 5 to 20 cm. It is intended to permit the catheter insertion through the cortex. It is designed to be inserted within the lumen of the ventricular catheter in order first to straighten the angulated tube and then spread out the ribs (103) by leaning on the inner part of the ventricular catheter tip (104) and therefore fold the membrane (102). The stylet's proximal end (121) is shaped in such a way to widen its proximal end and ease its handle, like a ring-shaped end for example.

III. Exemplary Methods for Installing the Catheter

A pair of exemplary methods for positioning the ventricular catheter is disclosed herein, depending on the use of either an introducer or a stylet, for example.

A. Method of Insertion Using an Introducer

After drilling a burr hole in the right parieto-occipital region or in the right frontal region, the cortex of the brain is cauterized then punctured with the introducer, which is gently headed to the ventricular junction. As shown in FIG. 4, in some embodiments the internal end (I) of the introducer is blunt to act as a canula for puncturing the cortex but is slotted so that it can provide passage to the ventricular catheter and then act as an open/close obturator to prevent excessive loss of CSF while puncturing the ventricle. Also shown therein, in some embodiments the introducer acts as a guide to the ventricles and/or as a constraining device capable of squeezing the flexible ribs (and therefore, to keep the semi-permeable membrane folded). The right positioning within the ventricle is demonstrated by the collection of CSF. The centimetric scale indicates the thickness of the cerebral parenchyma, and it allows one to choose the desired length of the ventricular catheter accordingly. Then, the ventricular catheter is introduced at the external opening of the introducer and slid in. Its progression is followed under control of the view through the transparent introducer. When the needed length of the ventricular length has been introduced, the introducer is gently slid out, which allows the distal end of the ventricular catheter to expand within the ventricle and the tube to return to its right angle configuration. Once the introducer is removed from the ventricular catheter, the external tube is cut at the right length to be adequately connected to the valve.

The introducer is sterile, disposable, transparent and/or scaled, in particular aspects.

B. Method of Insertion Using a Stylet

In specific embodiments, there is an exemplary method using a stylet. After drilling a burr hole in the right parieto-occipital region or in the right frontal region, the cortex is cauterized and then punctured with the ventricular catheter straightened by the stylet. The right positioning within the ventricle is demonstrated by the collection of CSF at its external end. Then, the stylet is removed, which allows the distal end of the ventricular catheter to expand within the ventricle and the tube to return to its right angle configuration. The catheter is connected to the valve.

REFERENCES

All patents and publications mentioned in the specification are indicative of the levels of those skilled in the art to which the invention pertains. All patents and publications are herein incorporated by reference to the same extent as if each individual publication was specifically and individually indicated to be incorporated by reference.

PATENTS AND PATENT APPLICATIONS

U.S. Pat. No. 5,531,673
U.S. Patent Publication No. 2006/0235439
U.S. Pat. No. 5,584,314

From the foregoing disclosure and detailed description of certain preferred embodiments, it will be apparent that various modifications, additions and other alternative embodiments are possible without departing from the true scope and spirit of the invention. The embodiments discussed were chosen and described to provide the best illustration of the principles of the invention and its practical application to thereby enable one of ordinary skill in the art to use the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A ventricular catheter comprising:
a tube for diverting cerebrospinal fluid, the tube having an extra-cerebral end and an intra-cerebral end;
a membrane having an apex and a connecting end opposing the apex, wherein the connecting end is attached to the intra-cerebral end of the tube; and
a plurality of memory ribs extending along a surface of the membrane from the connecting end to the apex,
wherein the ventricular catheter has a relaxed configuration in which the memory ribs spontaneously return to a pre-shaped conformation to expand a diameter of the membrane, and
wherein the ventricular catheter has a narrowed configuration in which the diameter of the membrane is smaller compared to the relaxed configuration.

2. The ventricular catheter of claim 1, wherein the membrane is semipermeable.

3. The ventricular catheter of claim 1, wherein the tube comprises one selected from the group consisting of latex, silicone, polytetrafluoroethylene (PTFE), and combinations thereof.

4. The ventricular catheter of claim 2, wherein the semipermeable membrane comprises one selected from the group consisting of polyacrylate, polyvinylidene, polyvinyl chloride copolymer, polyurethane, polystyrene, polyamide, cellulose acetate, cellulose nitrate, polysulfone, polyphosphazene, polyacrylonitrile, poly(acrylonitrile/covinyl chloride), PTFE, and combinations thereof.

5. A kit comprising
the ventricular catheter of claim 1, and
one selected from the group consisting of an introducer device for implanting the catheter in a subject, a stylet for implanting the catheter in a subject, and combinations thereof,
wherein the ventricular catheter is slidably houseable inside the introducer device,
wherein a stylet is inserted within the ventricular catheter.

6. The kit of claim 5, wherein the introducer device is cylindrical.

7. The kit of claim 5, wherein the introducer device at least partially encases the catheter.

8. The kit of claim 7, wherein the introducer device comprises one end that is slotted.

9. The kit of claim 5, wherein the kit comprises both the introducer device and the stylet.

10. The kit of claim 5, wherein the introducer device comprises one selected from the group consisting of metal, plastic, and combinations thereof.

11. A method of diverting cerebrospinal fluid from a brain ventricle of a subject via a tube for diverting cerebrospinal fluid, the tube having an extra-cerebral end and an intra-cerebral end;
a membrane having an apex and a connecting end opposing the apex, wherein the connecting end is attached to the intra-cerebral end of the tube; and
a plurality of memory ribs extending along a surface of the membrane from the connecting end to the apex,
wherein the ventricular catheter has a relaxed configuration in which the memory ribs spontaneously return to a pre-shaped conformation to expand a diameter of the membrane, and
wherein the ventricular catheter has a narrowed configuration in which the diameter of the membrane is smaller compared to the relaxed configuration,
the method comprising:
puncturing a brain cortex of the subject with an introducer device;
sliding the ventricular catheter, in a folded configuration through the introducer device up to the ventricular cavity, wherein when in the folded configuration the membrane is in a deflated shape;
removing the introducer from the brain cortex to expand the membrane to the relaxed configuration within the ventricular cavity; and
diverting cerebrospinal fluid of the subject through the tube.

12. The method of claim 11, wherein the subject is further defined as having hydrocephalus.

13. The method of claim 11, further comprising positioning a stylet within the catheter prior to the puncturing step.

14. The ventricular catheter of claim 1, wherein the membrane is permeable.

15. The ventricular catheter of claim 1, wherein the membrane is a coil-shaped serpentine membrane.

16. The ventricular catheter of claim 15, wherein the memory ribs extend around the membrane in a helix shape.

17. A method of diverting cerebrospinal fluid from a brain ventricle of a subject via a tube for diverting cerebrospinal fluid, the tube having an extra-cerebral end and an intra-cerebral end;
a membrane having an apex and a connecting end opposing the apex, wherein the connecting end is attached to the intra-cerebral end of the tube; and
a plurality of memory ribs extending along a surface of the membrane from the connecting end to the apex,
wherein the ventricular catheter has a relaxed configuration in which the memory ribs spontaneously return to a pre-shaped conformation to expand a diameter of the membrane, and
wherein the ventricular catheter has a narrowed configuration in which the diameter of the membrane is smaller compared to the relaxed configuration,
the method comprising:
inserting a stylet within a lumen of the ventricular catheter, wherein the stylet straightens the tube, spreads out the plurality of memory ribs, and folds the membrane by applying force to an inner part of the ventricular catheter;
puncturing a brain cortex of the subject;
sliding the ventricular catheter, in the narrowed configuration to a ventricular cavity of the brain ventricle;
removing the stylet from the ventricular catheter to expand the membrane to the relaxed configuration within the ventricular cavity; and
diverting cerebrospinal fluid of the subject through the tube.

* * * * *